(12) United States Patent
Erickson et al.

(10) Patent No.: US 7,665,605 B2
(45) Date of Patent: Feb. 23, 2010

(54) SHARPS CONTAINER FOR (I) SAFE DISPOSAL AND STORAGE OF A SINGLE USED MEDICAL PEN NEEDLE AND/OR (II) SAFE STORAGE AND DISPENSING OF A SINGLE UNUSED MEDICAL PEN NEEDLE

(75) Inventors: Thomas E. Erickson, Crosslake, MN (US); James J. Erickson, Mound, MN (US); Timothy A. Bachman, Saint Paul, MN (US)

(73) Assignee: UltiMed, Inc., St. Paul, MN (US)

( * ) Notice: Subject to any disclaimer, the term of this patent is extended or adjusted under 35 U.S.C. 154(b) by 109 days.

(21) Appl. No.: 10/918,756

(22) Filed: Aug. 14, 2004

(65) Prior Publication Data

US 2006/0032769 A1    Feb. 16, 2006

(51) Int. Cl.
*A61M 5/32* (2006.01)
*A61B 19/02* (2006.01)

(52) U.S. Cl. .................. 206/363; 206/367; 206/438; 206/571

(58) Field of Classification Search ......... 206/363–367, 206/571, 380, 438; 604/198, 263, 110, 192, 604/195; 220/839, 836, 837, 266, 831, 832; 215/235, 250, 258
See application file for complete search history.

(56) References Cited

U.S. PATENT DOCUMENTS

| | | | |
|---|---|---|---|
| 4,113,090 A * | 9/1978 | Carstens ..................... 206/365 |
| 4,347,946 A * | 9/1982 | Nichols ....................... 220/375 |
| 4,610,667 A * | 9/1986 | Pedicano et al. ............. 604/192 |
| 4,702,385 A | 10/1987 | Shilington et al. | |
| 5,409,113 A | 4/1995 | Richardson et al. | |
| 5,494,158 A | 2/1996 | Erickson | |
| 5,545,145 A | 8/1996 | Clinton et al. | |
| 5,605,254 A * | 2/1997 | Wagner et al. ............... 222/108 |
| 5,941,857 A * | 8/1999 | Nguyen et al. ............... 604/263 |
| 5,944,700 A * | 8/1999 | Nguyen et al. ............... 604/263 |
| 5,968,021 A * | 10/1999 | Ejlersen ....................... 604/263 |
| 5,971,966 A * | 10/1999 | Lav ............................ 604/263 |
| 5,996,779 A * | 12/1999 | Klardie et al. ............. 206/63.5 |

(Continued)

FOREIGN PATENT DOCUMENTS

EP    0 903 157 A2    3/1999

(Continued)

*Primary Examiner*—Mickey Yu
*Assistant Examiner*—Steven A. Reynolds
(74) *Attorney, Agent, or Firm*—Crompton, Seager & Tufte

(57) ABSTRACT

A sharps container for only one medical pen needle is configured with an elongated, hollow shield having an axially extending recess at a first end thereof. The recess is sized to receive the outer diameter of a pen needle hub. A cover member, sized for closing off the first end of the shield, is connected to the shield by means facilitating movement of the cover member between (i) a first position adjacent to a side of the shield and (ii) a second position abutting the first end of the shield. Locking means may be used for locking the cover member in the second position. The container has dual utilizations, first as a container for only one used medical pen needle and alternatively as a container for only one unused medical pen needle.

5 Claims, 3 Drawing Sheets

U.S. PATENT DOCUMENTS

| | | | |
|---|---|---|---|
| 6,332,534 B1 * | 12/2001 | Hammett | 206/366 |
| 6,685,017 B2 | 2/2004 | Erickson | |
| 6,926,179 B2 * | 8/2005 | Wagner et al. | 222/481.5 |
| 2002/0170912 A1 * | 11/2002 | Clarke | 220/254.1 |
| 2003/0121814 A1 | 7/2003 | Tan et al. | |
| 2005/0038392 A1 * | 2/2005 | DeSalvo | 604/198 |

FOREIGN PATENT DOCUMENTS

EP 1 138 338 A1 10/2001

* cited by examiner

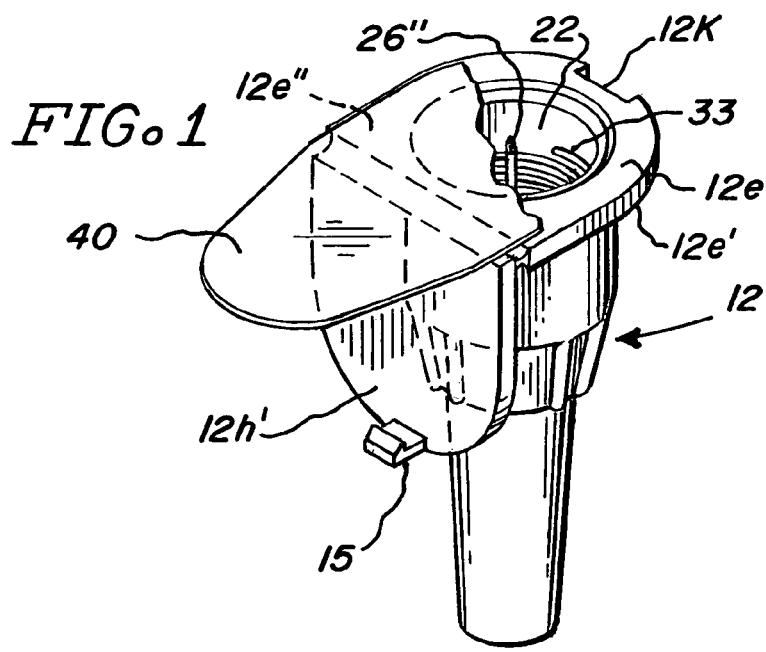
FIG. 1
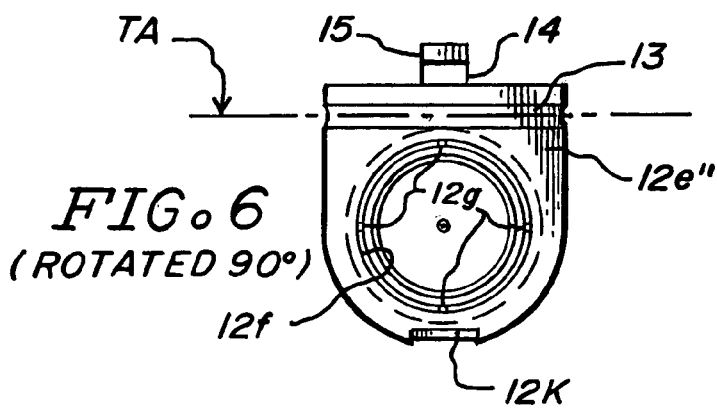
FIG. 6
(ROTATED 90°)
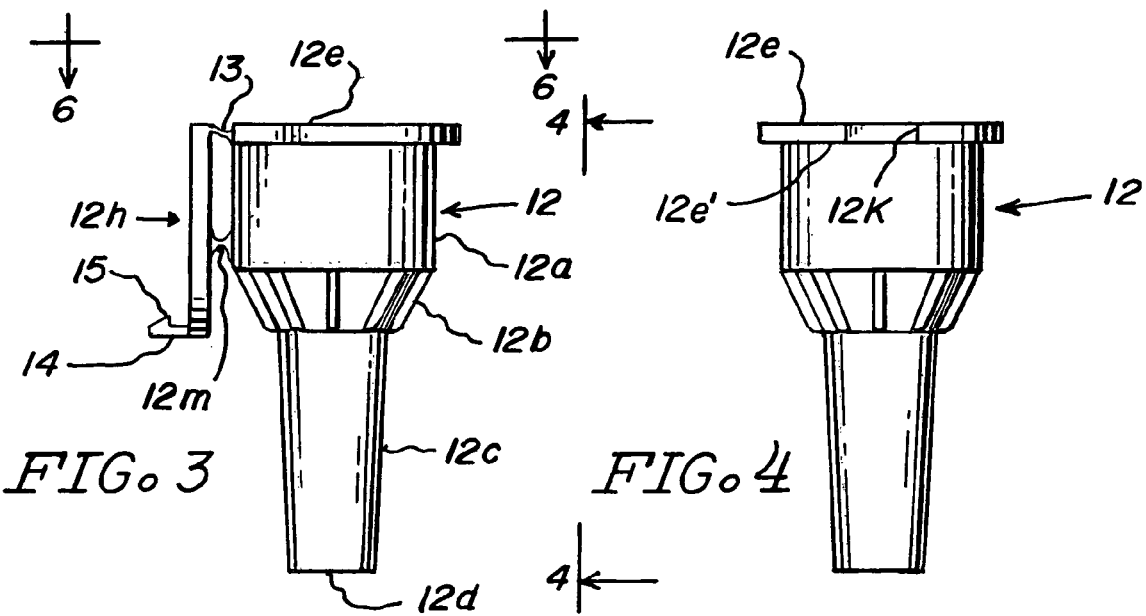
FIG. 3
FIG. 4

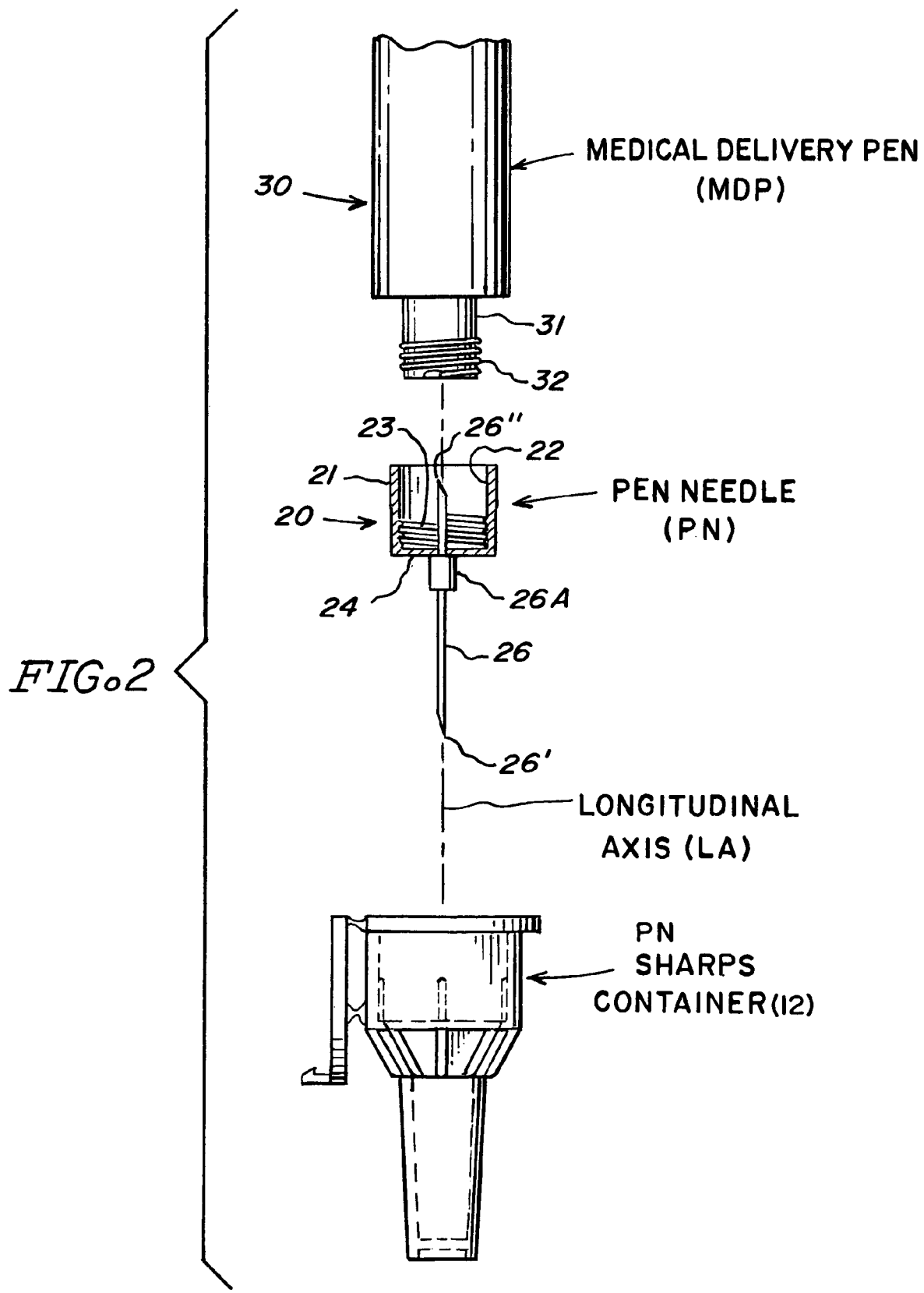

SHARPS CONTAINER FOR (I) SAFE DISPOSAL AND STORAGE OF A SINGLE USED MEDICAL PEN NEEDLE AND/OR (II) SAFE STORAGE AND DISPENSING OF A SINGLE UNUSED MEDICAL PEN NEEDLE

BACKGROUND AND FIELD OF THE INVENTION

This invention relates generally to a "sharps" container sized to receive or hold only one (a single) used medical pen needle (sometimes hereafter referred to as a "PN") and specifically to a sharps container sized to hold only one used PN which provides the safe (no-touch) insertion of said single PN into the container for safe storage therein. The container can also be used, initially, for the safe storage and dispensing of a single unused medical pen needle.

Because of well known health issues, the safe disposal of syringes and other "sharps" has long been a high priority for medical related professional facilities and industries. Prior art sharps containers are frequently found in public venues such as hospitals, medical clinics, and retail establishments. These containers are usually securely attached to some base means and may have a lock means to permit controlled and safe removal of used "sharps."

There are also prior art "portable" sharps containers for syringes, examples being U.S. Pat. Nos. 5,409,113; 5,494,158 and 6,685,017 showing sharps containers which necessarily are large because of the size of the elongated syringes.

Medical delivery pens (hereinafter sometimes "MDPs") have, more recently, become widely used instead of, or in addition to, syringes, e.g., by diabetics, who frequently inject themselves several times a day with accurately measured, adjustable, pre-selected amounts of insulin or other medication. MDPs are popular with many people for several reasons including the convenience of compact carrying cases which can fit into a purse or equivalent. Medical delivery pens include a reservoir of medication and a distal end adapted to be attached (usually by thread means) to a pen needle assembly (PNA). As is well known (see, for example FIG. 1 of U.S. Pat. No. 5,545,145), the pen needle assembly has a pen needle (PN) within an outer, generally cylindrical shield 28. The PN comprises a hub having a cylindrical wall extending axially from a radially extending bottom portion. An axially extending hollow needle 21 is centrally positioned on the bottom portion (i) the proximal end 24 of which punctures a seal in the distal end 16 of the medical delivery pen 10 (to allow the flow therethrough of medication) when the delivery pen is screwed into the proximal end of the pen needle cylindrical housing 26, and (ii) the distal end 22 of which is for insertion into tissue of the person requiring the medication. The pen needle assemblies typically include a removable thin sterile seal covering the proximal (large diameter) end of the said outer shield and a removable tube-like shield covering the distal portion of the hollow needle. The assembled pen needle assembly is then factory sterilized. The user of a pen needle assembly typically holds the PNA in one hand; removes the sterile seal from the outer shield; screws the distal end of the MDP into the proximal or hub end of the PN; removes the outer and tube-like shields from the PN; sets the medical delivery pen for the desired dose of medication; and then inserts the distal end of the hollow needle into the target tissue following which the MDP is actuated to deliver the desired dose of medication through the hollow needle into said tissue.

Many diabetics routinely administer medication to themselves several times a day by injection of a pre-selected quantity of insulin (or substitute medication) in liquid form. The correct amount of medication can be determined from prior professional medical instruction or by use of small, compact, and convenient portable blood analysis kits which provide rapid indicators of the user's blood sugar level. The several daily injections are often done away from the diabetic's primary home or residence which has fostered widespread use of the portable, convenient medical delivery pens. The aforesaid testing kits and the medical delivery pens are relatively small in size and, as indicated, can easily and conveniently accompany the person. A typical scenario for a diabetic at a restaurant is, prior to a mean, to first use the blood sugar testing kit to obtain an indicator of his or her blood sugar level. This information then facilitates programming or adjusting the medical delivery pen to deliver the desired quantity of medication. Then the MDP with an attached PN is used to inject the medication. These steps require a relatively short length of time and can be done with minimum loss of privacy.

MDPs are also widely used by doctors, nurses and other professionals in performance of their duties. Many individuals will request (sometimes insist) that an injection be done with a PN rather than a syringe. The aforementioned professionals are especially mindful of possible dangers from possible unwanted "sticks" that occur in the professional world.

In a perfect world, the user (both individual and professional) of a pen needle would, after the first use of a PN attached to a MDP, carefully detach the used PN from the MDP and safely dispose said used PN in a sharps container. The approved procedure is (i) insertion of the distal end of the needle of the PN into the tube-like shield (sometimes omitted) and thence the shielded needle and PN cylindrical housing (hub) into the outer shield (to form a PNA), (ii) unscrewing of the medical delivery pen from the proximal end of the pen needle cylindrical housing, and (iii) careful placement of the "used" PNA into a safe sharps container.

Alas, the recommended procedure is not always followed. Used (and potentially dangerous) PNs or PNAs are routinely left in unsafe places where third parties may unwittingly be "stuck." Examples of such unsafe places are purses, the pockets on the back of aircraft seats, private and public wastebaskets, garbage cans, dumpsters and empty milk or other unsafe containers.

Further, the above described disposal procedure requires that the MDP user (or associate) handle or hold the PN while the MDP is unscrewed therefrom. This creates the possibility of a potentially dangerous "stick." Further, if the user (or associate) tries to insert the used PN into the outer shield to form a PNA, then additional handling is again required with the possibility of a "stick"

One prior art example of a container for unused and used pen needle assemblies is U.S. Pat. No. 5,545,145 which shows a tube containing a small number of unused pen needle assemblies arranged in axial alignment. This patent also teaches that, as unused assemblies are removed from one end of the tube, then a used assembly may be inserted into the tube from the other end. The tube is adapted to be attached to the side of a medical delivery pen. This arrangement has significant shortcomings. Potentially dangerous "sticks" could occur when a user (or associate) tries to insert a used PN (with or without the protective outer shield) into the used end of the tube.

The present invention provides a totally "no-touch" means for a MDP user of PNs to transfer a used PN from a MDP into a unique used PN sharps container for safe storage therein without, as indicated, any touching of the used PN by the user. Providing a small, compact and safe sharps container for only one, i.e., single used PN has significant cost and functional advantages as compared with the much larger and thus somewhat cumbersome prior art "bulk" sharps containers. Alternately, the same container may be used, in combination with a MDP, as a container for a single unused medical pen needle.

SUMMARY OF THE INVENTION

This invention provides a sharps container for only one medical pen needle. The container is configured with an elongated, hollow shield having an axially extending recess at a first end thereof. The recess is sized to receive the outer diameter of a pen needle hub. A cover member, sized for closing off the first end of the shield, is connected to the shield by means facilitating movement of the cover member between (i) a first position adjacent to a side of the shield and (ii) a second position abutting the first end of the shield. Locking means may be used for locking the cover member in the second position. The container has dual utilizations, first as a container for the disposal and storage of one used medical pen needle and alternatively as a container for the storage and dispensing of one unused medical pen needle. The container is intended for use in combination with a medical delivery pen. The recess in the hollow shield has a plurality of axially extending ribs sized and circumferentially oriented to receive axially extending shallow recesses on the outer surface of the medical pen needle hub. Thus a used medical pen needle attached to a medical delivery pen may be inserted into the recess; the ribs and shallow recesses coact to prevent rotation of the pen needle while the MDP is unscrewed from the PN.

Alternately, an unused PN stored in the recess of the hollow shield is held against rotation by the ribs and shallow recesses while a MDP is screwed into the hub of the PN. Then the MDP may extract the unused PN for its use in administering a medication.

DESCRIPTION OF THE DRAWINGS

FIG. 1 is an isometric top, left view of a sharps container for only one medical pen needle, this view showing an unused medical pen needle positioned in the sharps container, a hygienic seal being partially cut away.

FIG. 2 is an exploded view of the sharps container of FIG. 1 (sans the PN and the hygienic seal) in combination with a PN (in cross-section) and a MDP all in alignment with a longitudinal axis LA.

FIG. 3 is a side view of the container.

FIG. 4 is a right side view of the container as viewed along section lines 4-4 of FIG. 3.

FIG. 6 is a view of the proximal end of the container as viewed along section lines 6-6 of FIG. 3.

DETAILED DESCRIPTION

Figure 5:
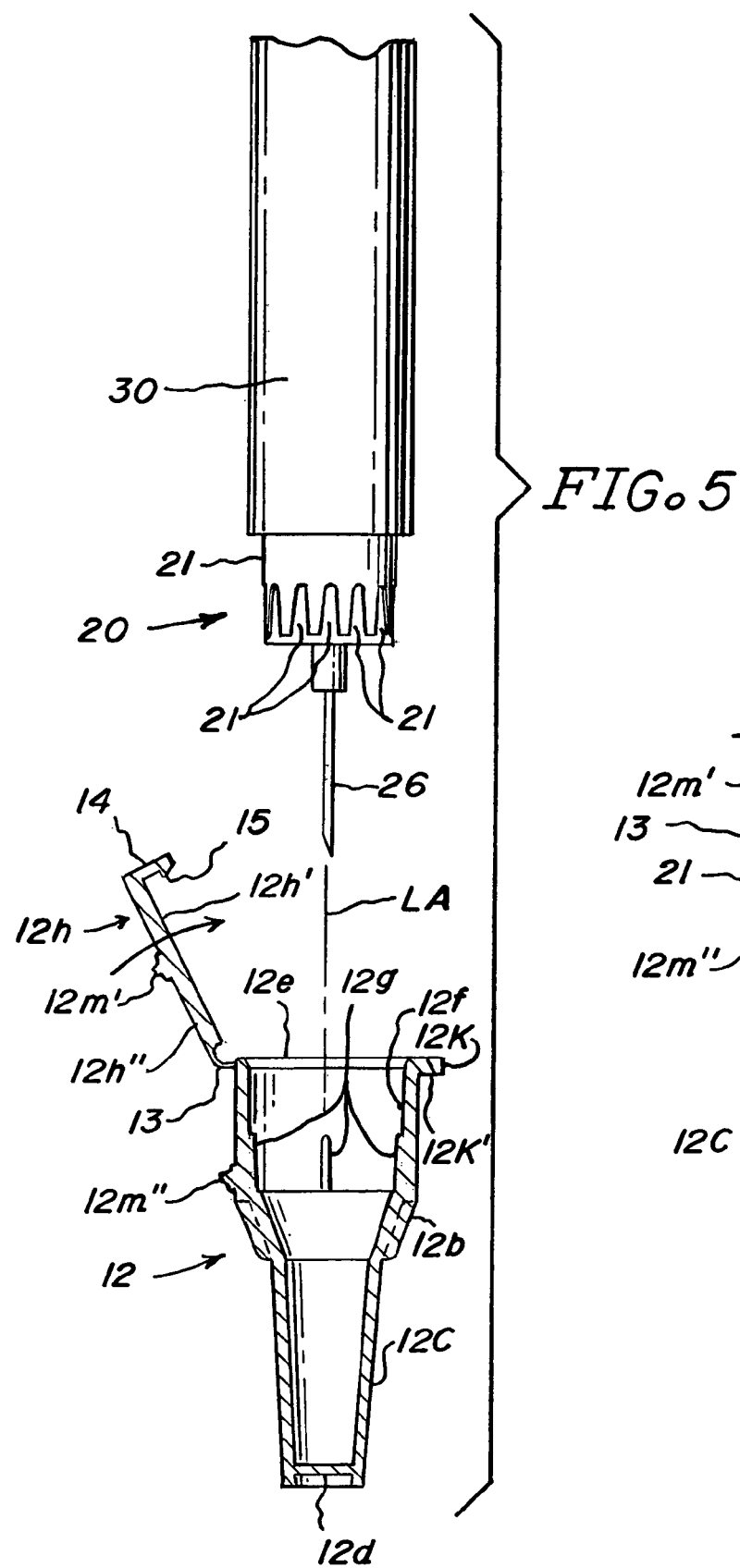
FIG. 5 is an exploded view of the sharps container (in cross-section) in combination with an assembled PN and MDP.

In FIG. 1 a sharps container or shield 12 is shown in a first of two alternate utilizations, i.e., providing a means for the safe (no direct human touching) storage and dispensing of a single unused medical pen needle (PN) 20 to be connected to the distal end of a medical delivery pen (MDP) 30 (see FIG. 2). The sharps container or shield 12 as shown in FIG. 2 depicts the other or second utilization, i.e., the safe disposal and storage of a single used medical pen needle. In the preferred embodiment, the shield is made of a suitable plastic by extrusion process.

Referring to the drawings, the shield 12 is a generally cylindrically shaped, elongated, hollow member having a first axially extending portion 12a extending from a first, open, proximal end 12e. An axially extending recess 12f (see FIG. 5) is provided at end 12e and is sized to receive the outer cylindrically shaped surface 21 of the hub of PN 20.

Figure 7:
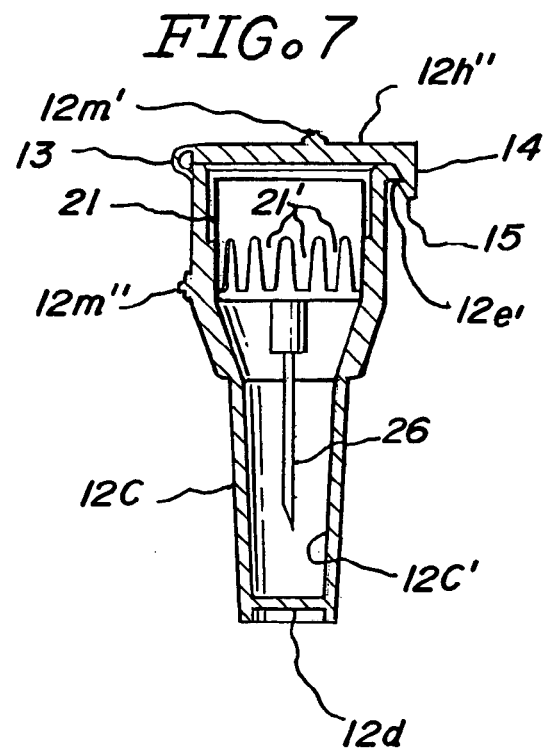
FIG. 7 is a side view of the sharps container (in cross-section) within which is positioned one used PN, a cover member being locked in a position abutting the proximal end of the container to thereby safely store the used PN.

A typical medical PN 20 is shown in FIGS. 1, 2, 5 and 7. The outer cylindrical surface 21 of the PN has a plurality of axially extending, shallow recesses 21' which are circumferentially oriented to mate with axially extending rib means 12g integral with the recess 12f when the hub of the PN is positioned in the recess as shown in FIGS. 1 and 7. The ribs 12g and shallow recesses 21' co-act to prevent relative rotation between the container 12 and the PN when the MDP is either in the dispensing or the disposal modes of utilization.

The container or shield 12 has sufficient longitudinal length so that a PN may be entirely housed therein (see FIG. 7) and may, after portion 12a, be of reduced diameter as indicated by successive longitudinal sections 12b and 12c shown in FIG. 3, the other, or second, distal end 12d of the shield 12 being closed off.

Additional details of PN 20 are shown in FIG. 2. The cylindrically shaped outer surface 21 of the hub extends axially from a bottom, radially extending surface 24 in which is centrally positioned and mounted an axially extending hollow needle means 26. The proximal end of the hub 21 is open thus defining a recess 22 with female thread means 23 sized to receive and mate with the male thread means 32 on the distal end 31 of the MDP 30.

The hollow needle means 26 has a shoulder-like portion 26a adjacent to surface 24, a distal pointed tip 26' and a proximal pointed tip 26". The tip 26" has an axial length pre-selected to be enclosed within the recess 22 (see FIG. 2). As is well known and as discussed above, when a MDP is to be used to administer a medication, the distal threaded end 31/32 thereof is screwed into the female threaded recess 22/23 of the PN which forces the proximal tip 26" of the needle means 26 to puncture a membrane within the MDP to thus facilitate the transfer of medication (held within the MDP by the membrane) via the hollow needle 26 and exiting at the distal tip 26' into the tissue of the recipient.

The proximal end 12e of shield 12 has a radially extending surface which is flat or planar as is clearly shown in the drawings. A radially extending shoulder 12e' at end 12e increases the area of said surface. The shoulder 12e' includes a radial extension 12e" shown best in FIGS. 1 and 6 and which provides a connection for a hinge means 13 linking a flat-like cover member 12h to shield 12.

Cover member 12h has inner and outer surfaces 12h' and 12h" respectively and is sized so that it can completely seal off or close off the open, proximal end 12e of shield 12 (see FIG. 7 where the inner surface 12h' abuts end 12e). In the preferred embodiment of our invention the cover member 12h is initially positioned adjacent the side of shield 12 (see FIGS. 1, 2 and 3). A break-away link 12m may be provided to hold the cover member 12h adjacent to the side of the shield portion 12a (see FIG. 3), i.e., to hold the cover in a first position (relative to the shield) until the link 12m is manually broken or disabled prior to the manual rotation of the cover member to a second position covering the end 12e of the shield. The link 12m, after being broken, has residual portions 12m' and 12m" attached to the side of shield 12 and the surface 12h" of the cover member respectively.

The hinge means 13 facilitates the aforesaid selective, manual rotation or movement of the cover member 12 from the first position to the second position. The hinge means 13 and cover member 12h are preferably made of the same plastic material as shield 12.

The sharps container preferably includes a locking means for locking the cover member to the end 12e of the shield when the cover member is in the aforesaid second position. The locking means includes (i) a notch 12k in the shoulder 12e' positioned opposite the hinge means 13 and (ii) a latch means 15 connected by a short shoulder 14 to the end of cover member 12h opposite the hinge means as is clearly shown in the drawings. When the cover member 12h is manually moved into the second position as depicted in FIG. 7, the latch means 15 will be in register with the notch 12k and engage the underside of the shoulder 12e' to thereby lock the cover member 12h against the open end 12e and thus safely store within a used PN.

In the operation and use of our sharps container as a means for the safe storage and dispensing of a single unused medical PN, the unused PN would be provided to the user in the mode depicted in FIG. 1 where a hygienic seal 40 is attached to the end 12e of the shield 12 after the unused PN is positioned therein, the assembled items then being factory sterilized. When desired, the user would selectively remove the seal 40, insert and attach (by rotation) the distal end 31/32 of the MDP to the recess 22/23 of the PN, then axially withdraw the PN from the shield 12 for the aforesaid administration of medication. Thus our sharps container has facilitated the safe storage and dispensing of a single unused PN.

In the use of our sharps container as a means for the safe disposal and storage of a single used PN attached to the end of a MDP as shown in FIG. 5, the MDP would be manipulated so that the needle 26 would be first inserted into the hollow shield and thence the hub of the PN would be positioned in the recess 12f. The ribs 12g would be in the shallow recesses 21' to prevent relative rotation between the PN and the container. The user then merely unscrews the MDP from the PN and withdraws the MDP. The cover member 12h is then rotated or moved to the "second" position and locked to the shield at end 12e thereof as is shown in FIG. 7. The single used PN is thus safely disposed and stored in our sharps container.

The user of our sharps containers may, of course, first use a specific container for the dispensing of a single unused PN for the MDP administration of a desired amount of medication and then use the same container for the safe storage and disposal of the PN. In some cases the user could carry a plurality of our sharps containers in a purse or pocket or equivalent means.

While we have described the preferred embodiment of our invention, it will be understood that variations may be made by those skilled in the art without departing from the inventive concept. Accordingly, the invention is to be measured only by the scope of the following claims.

What is claimed is:

1. A sharps container for facilitating the safe storage and dispensing of only one unused medical pen needle comprised of (i) a hub having a cylindrical wall extending axially from a bottom radially extending surface, (ii) a plurality of axially extending shallow recesses on an outer surface of said cylindrical wall, (iii) female thread means on an inner surface of said cylindrical wall and (iv) needle means centrally connected to said bottom surface and having distal and proximal ends extending axially from said bottom surface, said container comprising:

a. an elongated generally cylindrical, hollow shield having a longitudinal axis and an axially extending recess at a first end thereof, said recess being sized to receive the outer diameter of a pen needle hub and said shield having a closed second end and a longitudinal extent preselected to facilitate holding therein an unused pen needle;

b. a cover member sized for closing off said first end of said shield, said cover member being connected to said shield by hinge means providing for rotation of said cover member about a transverse axis relative to said shield, the rotational axis of said hinge lying in a plane substantially parallel to the plane of the first end of said shield to facilitate movement of said cover member between (i) a first position adjacent to said cylindrical shield and parallel to the longitudinal axis of said cylindrical shield and (ii) a second position abutting said first end of said shield, said cover member further including locking means for locking said cover member in said second position;

c. a removable hygienic seal means connected to said first end of said shield, whereby (i) said seal means may be manually removed from said first end of said shield and (ii) the threaded distal end of a medical delivery pen may be screwed into said female thread means of an unused medical pen needle positioned within said container to facilitate the manual axial withdrawal of said medical pen needle from said container, and d. a holding member disposed on said side of said shield and being attached to said cover member to hold said cover member in said first position, said holding member being breakable from said shield so that said cover member can be manually moved from the first position in which the cover is held to the second position in which the cover is locked.

2. The sharps container of claim 1 wherein said locking means includes means integral with said cover member.

3. The shams container of claim 1 wherein said recess has axially extending rib means sized and circumferentially oriented to receive said axially extending shallow recesses on said outer surface of said cylindrical wall of said pen needle hub, whereby a unused pen needle positioned in said container may be attached to a medical delivery pen inserted into said recess and said unused pen needle being held therein against angular rotation by the co-action between said rib means and said axially extending shallow recesses to thereby facilitate the (i) the safe attachment of said medical delivery pen to said unused pen needle and (ii) the safe dispensing of said unused pen needle by manual axial withdrawal of said medical delivery pen relative to said container.

4. The shams container of claim 3, whereby a used pen needle positioned in said container may be removed from a medical delivery pen inserted into said recess, said unused pen needle being held therein against angular rotation by the co-action between said rib means and said axially extending shallow recesses to thereby facilitate the (i) the safe detachment of said medical delivery pen from said used pen needle and (ii) the safe disposal of said unused pen needle by manual axial withdrawal of said medical delivery pen relative to said container with subsequent locking of the cover thereof.

5. The shams container of claim 1 wherein said shield has a second end having a diameter smaller than the diameter of said first end of said shield.

\* \* \* \* \*